United States Patent
Davis

(10) Patent No.: US 7,749,164 B2
(45) Date of Patent: Jul. 6, 2010

(54) SYSTEM AND METHOD FOR THE PROCESSING OF ALARM AND COMMUNICATION INFORMATION IN CENTRALIZED PATIENT MONITORING

(75) Inventor: Carl C. Davis, Menomonee Falls, WI (US)

(73) Assignee: The General Electric Company, Schenectady, NY (US)

( * ) Notice: Subject to any disclaimer, the term of this patent is extended or adjusted under 35 U.S.C. 154(b) by 553 days.

(21) Appl. No.: 11/426,992

(22) Filed: Jun. 28, 2006

(65) Prior Publication Data

US 2008/0004499 A1 Jan. 3, 2008

(51) Int. Cl.
*A61B 5/00* (2006.01)
(52) U.S. Cl. ............... 600/300; 705/2; 128/920
(58) Field of Classification Search ......... 128/903–905, 128/920; 340/539.12–539.13, 573.1
See application file for complete search history.

(56) References Cited

U.S. PATENT DOCUMENTS

| 5,331,549 | A |   | 7/1994 | Crawford, Jr. |   |
|---|---|---|---|---|---|
| 6,024,699 | A | * | 2/2000 | Surwit et al. | 600/300 |
| 6,301,503 | B1 |   | 10/2001 | Hsu et al. |   |
| 6,369,705 | B1 |   | 4/2002 | Kennedy |   |
| 6,544,174 | B2 | * | 4/2003 | West et al. | 600/300 |
| 6,804,656 | B1 |   | 10/2004 | Rosenfield et al. |   |
| 6,941,167 | B2 |   | 9/2005 | Stahmann et al. |   |
| 2003/0117296 | A1 |   | 6/2003 | Seely |   |
| 2005/0242946 | A1 |   | 11/2005 | Hubbard, Jr. et al. |   |
| 2006/0064020 | A1 |   | 3/2006 | Burnes et al. |   |

FOREIGN PATENT DOCUMENTS

EP 0 569 670 A2 11/1993

OTHER PUBLICATIONS

LiveData website page.
Visicu website page.
"IntelliVue Information Center with portal technology", Phillips Medical Systems, Jan. 2005.
IntelliVue Information Center—Instructions For Use, Document No. M3150-9201D, Phillips Electronics North America Corp., 2001, 2002.
Search Report dated Sep. 4, 2007.

* cited by examiner

*Primary Examiner*—Michael C Astorino
(74) *Attorney, Agent, or Firm*—Andrus, Sceales, Starke & Sawall, LLP

(57) ABSTRACT

A system and a method allowing a technician to monitor the condition of a plurality of patients and communicate their condition to an attending clinician. A centralized receiving station receives signals from each of the patients being monitored. A graphical user interface simultaneously displays an indication of patient condition for each of a plurality of patients. A technician utilizes this information to efficiently communicate the conditions of the patients to an attending clinician.

16 Claims, 3 Drawing Sheets

FIG. 2

| PATIENT | TIME | 12:24 | 12:22 | 12:20 | 12:18 | 12:16 | 12:14 |
|---|---|---|---|---|---|---|---|
| BETA, ALPHA | 3 | WARN | ◈ | ◈ CRITICAL | | ◈ | |
| PAST, PRESENT | 7 | | | | WARN | ◈ | |
| DAVIS, CARL | – – | | | | | | |
| WINNER, LOSER | 3 | CRITICAL | ◈ | | | ◈ WARN | |
| TICKING, CLOCK | – – | | | ◈ | | | |
| UNIT 1, BED 1 | 5 | | CRITICAL | ◈ | WARN | ◈ | |
| UNIT 1, BED 2 | – – | | | | | | |
| UNIT 1, BED 3 | | | | | | | |

FIG. 3

| PATIENT | TIME | 12:26 | 12:24 | 12:22 | 12:20 | 12:18 | 12:16 |
|---|---|---|---|---|---|---|---|
| BETA, ALPHA | – – | ◈ | WARN | ◈ | ◈ CRITICAL | | ◈ |
| PAST, PRESENT | 8 | | | | | WARN | ◈ |
| DAVIS, CARL | – – | | | | ◈ | | |
| WINNER, LOSER | – – | | ◈ CRITICAL | ◈ | | | ◈ WARN |
| TICKING, CLOCK | 6 | | | | ◈ | | |
| UNIT 1, BED 1 | – – | | | | CRITICAL | ◈ | WARN |
| UNIT 1, BED 2 | | | | | | | |
| UNIT 1, BED 3 | | | | | | | |

SYSTEM AND METHOD FOR THE PROCESSING OF ALARM AND COMMUNICATION INFORMATION IN CENTRALIZED PATIENT MONITORING

FIELD OF THE INVENTION

The present invention is a system and method for use in the field of biotelemetry. More specifically, the present invention is directed towards the management of patient care from a centralized location.

BACKGROUND OF THE INVENTION

In the healthcare system, clinician-patient interaction time is at a premium. In such an environment, when critical care is needed, clinician response time to the situation is critical. Systems of centralized monitoring have been developed to better manage clinician time and patient interaction. In centralized monitoring, physiological data from each patient is transmitted to a centralized location. At this centralized location, a single or small number of technicians receive all of this patient information and determine the patient's condition. Any patient parameter alarm signals that may be activated are sent to this centralized location to be viewed by the technician. The technicians use this information to determine the order and priority in which the clinicians should treat each patient. The technician then communicates the priority to the clinician using a variety of established communication means. These means may include wireless pagers, cell phones, notifying a floor or wing secretary, or making a hospital-wide audio page.

The technicians serve a variety of functions in processing the patient information as it is received to determine the patient's condition. Technicians filter the received patient information for artifacts or false alarms that would otherwise waste the clinician's valuable time. The technicians also prioritize and/or escalate the patient conditions such that the clinicians treat the patients first that are in most need of care.

Despite the important role in hospital care management that these technicians play, the current state of the technician work environment is less than desirable. The centralized monitoring station or "war room", as it is commonly referred to, will often have multiple work stations with multiple technicians working at a time. Each work station has multiple displays where patient data is displayed for each of the patients for which the technician is responsible.

In an example of a typical monitoring station, each technician may be responsible for approximately 48 patients, however, this number varies from institution to institution. Typically, a clinician will provide care to four patients at a time, once again more or less depending on the specific institution. Therefore, it is not uncommon for a single technician to have to keep track of the changing condition of 48 patients and relay these changes of condition to the proper one of twelve clinicians to provide the care to a specific patient. Although this task by itself is complicated enough, another important duty of the technician is to continue informing a clinician of the patient needs until the clinician has responded to that patient condition.

The proper clinician notification requires that the technician remember which clinicians have been notified of what patient conditions and whether or not the clinician has responded to the communication to indicate that treatment has been conducted for that patient. Many technicians must resort to paper notes and other mental organizational strategies to keep all of this data properly organized. The final task that the technician must perform is the evaluation and escalation of patient condition needs. These are often complex decisions that must weigh the need of a patient with a more severe condition to be treated versus a patient with a less severe condition but has not received treatment for a longer duration. The escalation decisions made by the technician are typically based upon a set of rules that are defined by the institution. However, since the process is not automated, the technician must resort to his or her knowledge of these institutional rules with which to make these treatment escalation decisions.

There is currently no automated system that keeps track of technician-clinician communications. Therefore, the technician must rely upon personal organizational and mental skills to process and monitor the clinician-patient interactions. Therefore, an organizational system that provides the necessary information to the technician in a single display is desirable in the field of patient care management. It is further desirable in the field of patient care management to provide an automated system that assists the technician in the escalation of the communication of patient treatment needs based upon an institutionally defined set of rules. It is still further desirable in the field of patient care management to provide an automated system that aids in the technician's analysis of patient physiological data.

SUMMARY OF THE INVENTION

The present invention provides a system and method of monitoring the condition of patients and the communications between a technician and a clinician in a single informative display. This single display uses alpha-numeric information as well as graphical representations to display the necessary information to the technician in intuitive fashion. The present invention provides the ability to track and monitor technician-clinician communication. In the present invention, the technician is aided by the automated application of institutional escalation rules. As another aspect of the present invention, the monitoring system provides a predictive feature of indicating the next expected actions by the technician and clinician.

BRIEF DESCRIPTION OF THE DRAWINGS

The drawings illustrate the best mode contemplated of carrying out the invention.

In the drawings:

FIG. 2 is a display of an embodiment of the present invention;

FIG. 3 is a display of an embodiment of the present invention; and

DETAILED DESCRIPTION

Figure 1:
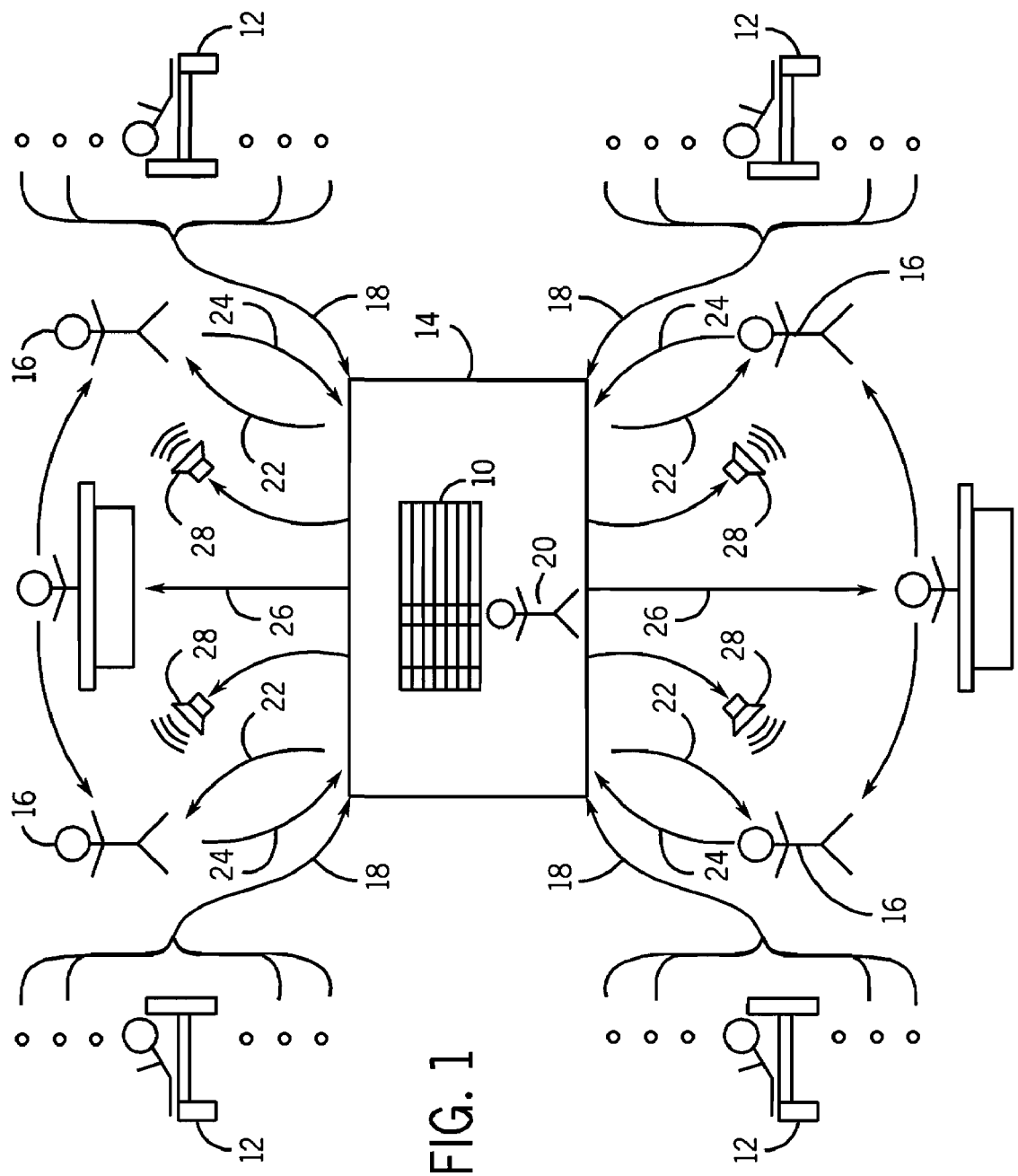
FIG. 1 is a schematic diagram of a centralized monitoring system implying an embodiment of the present invention.

FIG. 1 is a schematic diagram of the operation of a centralized monitoring system using the monitoring display 10 as an embodiment of the present invention. The centralized monitoring system comprises a plurality of patients 12 potentially at multiple locations, some locations being distant from the central monitoring station 14. Associated with each of the groups of patients 12 is an attending clinician 16 who is responsible for providing the treatment and care to the patients 12. Physiological data from each of the patients 12 is sent via a transmission means 18 to the central monitoring station 14. The transmission means 18 may utilize wired and/or wireless data transmission technology as this would be dictated by the institution(s) and the network infrastructure of the institution(s).

Computers (not pictured) of the central monitoring station 14 process the patient physiological data and display the data on a monitoring display 10 to the technician 20. The technician 20 monitors the physiological condition of the patients 12 via the monitoring display 10 as will be described further herein. The technician 20 monitors the progress of the patients 12, reviewing any alarm signals that are sent for verification of the patient's condition. After verifying the received alarm, the technician 20 will notify the clinician 16 via a communications transmission 22. This communications transmission 22 may be in the form of a page or a call on a landline or cellular phone, a text-based messaging system, or any other similarly suited person-to-person communications platform. In the central monitoring system depicted in FIG. 1, the technician 20 has no way of knowing whether or not the clinician 16 has responded to the communications transmission 22 by providing care to the patient 12, other than when the clinician responds to the communication transmission 22 with the clinician's own response transmission 24. Once the response transmission has been received by the technician 20 at the central monitoring station 14, the response is indicated as received on the monitoring display 10. The technician 20 now has a visual record that the clinician 16 has provided, or is providing, care in response to that patient alarm.

If, however, the clinician 16 does not send a response transmission 24, the technician 20 must follow a series of communication escalation rules that are defined by the particular institution to escalate the communication of that patient's alarms. In response to the escalation, the technician 20 will move to an escalated communications transmission such as a repeated paging attempt, wide-group paging (i.e. paging all of the nurses on a floor), contact desk notification 26, and/or overhead speaker calls 28. Similarly, after these notifications when the clinician 16 provides treatment to the patient 12, the clinician will send a response transmission 24 back to the central monitoring station 14, thereby notifying the technician that the patient 12 has received care and that the technician 20 need not escalate the communications transmissions further.

Referring now to FIG. 2, one embodiment of the monitoring display 10 of the present invention is depicted. The display includes a patient column 30 listing the names, and/or identifiers for each of the patients to be monitored by the technician at that time. Each row of data displayed on monitoring display 10 corresponds with the patient identified in patient column 30. The most prominent feature of the monitoring display 10 is the patient history display section 32. The patient history display section 32 is ordered in chronological order with the most recent refreshment of the patient history display 32 appearing at the left-hand side most proximal to the patient column 30. While the patient history display 32 may be a series of increments, as depicted in FIG. 2 (refreshing every two minutes), the refresh rate may be any rate as determined sufficient by the specific institution, including, but not meant to be limiting, information display in real time.

If a patient alarm is activated, then an alarm indicator 34 will be displayed in that patient's row in the patient history display 32. The alarm indicator 34 may be color or alphanumerically coded to display the level of importance of the alarm, and may also display specific alarm information (not pictured). The specific alarm information may include identification of the active alarm, or a display of that current patient physiological parameter. As such, the technician will receive a visual representation of the current active patient alarms, when the alarm began, and the level of importance of the alarm, which will affect the technician's decision to notify the clinician to treat the patient.

Once the technician has initiated a communications transmission to the proper clinician in response to a patient alarm signal, the patient history display 32 will display a communication sent indicator 36. If the clinician responds to the communication transmission by the technician, with the clinician's own response transmission, then the patient history display 32 will display a communication received indicator 38. Thus, by looking at the patient history display 32, the technician can quickly discern which communications have been sent in response to new patient alarms, and which response transmissions have been received in response to those communications transmissions. If no response transmission is received, then the alarm signal may escalate requiring the technician to send an additional communication transmission which would result in the patient history display 32 displaying another communication sent indicator as represented by indicator 40.

The monitoring display 10 also includes a "next action" column 42. In the next action column 42, the monitoring system of the present invention predicts based off of standard work flow operations the next expected communication action to be performed in relation to that patient in the central monitoring system. For example, patient Past, Present in the central monitoring system is currently experiencing a "warn" alarm as depicted by alarm indicator 44. The technician has initiated a communication transmission, and this has been recorded on the patient history display 32 as indicator 46, but as of yet has not received a response transmission from the attending clinician. Therefore, the next action that the technician expects to receive is a response transmission, and as such, a communication received indicator 48 is displayed in the next action column 42.

In further example, patient Beta, Alpha had been experiencing a critical alarm as indicated on the patient history display 32 by the alarm indicator 34. The technician sent a communication transmission as indicated by the communication sent indicator 36, and received a response transmission as indicated by communication received indicator 38. Shortly thereafter, the critical alarm ended leaving patient Beta, Alpha in a no alarm condition. Therefore, no next communication action is necessary at this time and therefore the corresponding spot in the next action column 42 is empty.

FIG. 3 depicts the same monitoring display 10 as depicted in FIG. 2, however, the display is two minutes later and as such the display has refreshed by one increment, displaying newly updated information. Referring to the previous example, the communication transmission sent by the technician to a clinician in response to patient Past, Present alarm condition has been received by the clinician has responded to the communication with a response transmission, indicated as indicator 50. Because the communication has been responded to by the clinician and because the alarm condition 44 has ceased, there is no "next action" indication in the "next action" column 42. As a final example, in FIG. 3, the patient Beta, Alpha has just begun to experience a critical alarm condition as depicted by alarm indicator 52. As the technician has not as of yet initiated a communication transmission, no communication sent indicator is depicted in the patient history display for this patient, but the communication sent indicator 54 does appear in the "next action" column 42. This identifies to the technician that the next communication action to be performed is by the technician and that the technician must send a communication transmission to the clinician.

Referring now back to FIG. 2, a metrics column 56 is disposed between the patient column 30 and the patient history display 32. The metrics column 56 displays patient-related metrics that are either institutionally defined or are selected by the technician for additional information to be displayed by the monitoring display 10. In the embodiment depicted in FIGS. 2 and 3, the metric displayed is the time since the first communication was initiated by the technician. The metrics column 56 presents another tool for the technician to determine the clinician response time as well as providing a useful tool for analysis of whether an alarm condition should be escalated. However, the metric column 56 could display a variety of other metrics or multiple metrics at once. The metrics displayed in the metrics column could comprise the time since the last communication, time from the alarm initiation, time since the last alarm condition, or length of the last alarm condition. This listing of potential metrics is in no way meant to be limiting upon the types of metrics that may be displayed in this column as the metrics need not be time based and could be any of a variety of patient physiological or hospital scheduling metrics as well and be regarded as within the present invention.

Further embodiments of the present invention may include the use of more detailed icons or other display options such as shading or shadowing to convey a greater amount of information to the technician in a simplified format. As an illustrative example, an icon may by used to indicate the type of communication that was made between the technician and the clinician, such as whether the communication was by alpha-numeric pager, cell phone, a third party, or a speaker. Other icons may indicate the direction of the communication either from the technician or from the clinician. Still other display options may include the indication of patient condition escalation or patient condition improvement, or an effect such as shading may be used to indicate that a patient has been temporarily removed from the monitored area of the hospital but is expected to return.

In further embodiments of the present invention, other data quantities besides patient alarms may be monitored and displayed to the technician. This data may include the specific location of patients within the institution, as a patient may be moved to various areas of the institution for necessary treatment or therapy. In such a case, an embodiment of the present invention would have the next action indicated as the need to put the patient back online for patient monitoring. Other data quantities being monitored could be broader institutional quantities such as the organization of patients by room, or the number of available beds in a specific area of the institution. Still further embodiments of the present invention may include more detailed analysis than a simple indication of alarm, such as providing a brief statement or alpha-numeric indication of the patient physiological parameter that caused the alarm.

Other embodiments of the present invention rely upon the implementation of a series of institutionally defined escalation rules that the system of the present invention may implement automatically to determine the patient alert escalation. An example of such an institutional rule may be that upon first indication of an alarm, the technician places an alpha-numeric page to the clinician. If the page is not responded to by the clinician within three minutes, then a cell phone call to the clinician is made by the technician. Further, if this cell phone call is not answered by the clinician within three more minutes, then an announcement for the clinician to proceed to the patient with the alarm may be made over the institution's intercom. This example is meant to be exemplary in nature and is not meant to be limiting upon the types and complexity of the escalation rules that may be implemented by an institution in accordance with the present invention. It is regarded that embodiments within the present invention may include other platforms of person to person communication, repeating of communication attempts, or any specific lengths of time intervals between communication attempts or communication escalations, however these embodiments are merely exemplary and not meant to be limiting to the scope of the present invention.

Figure 4:
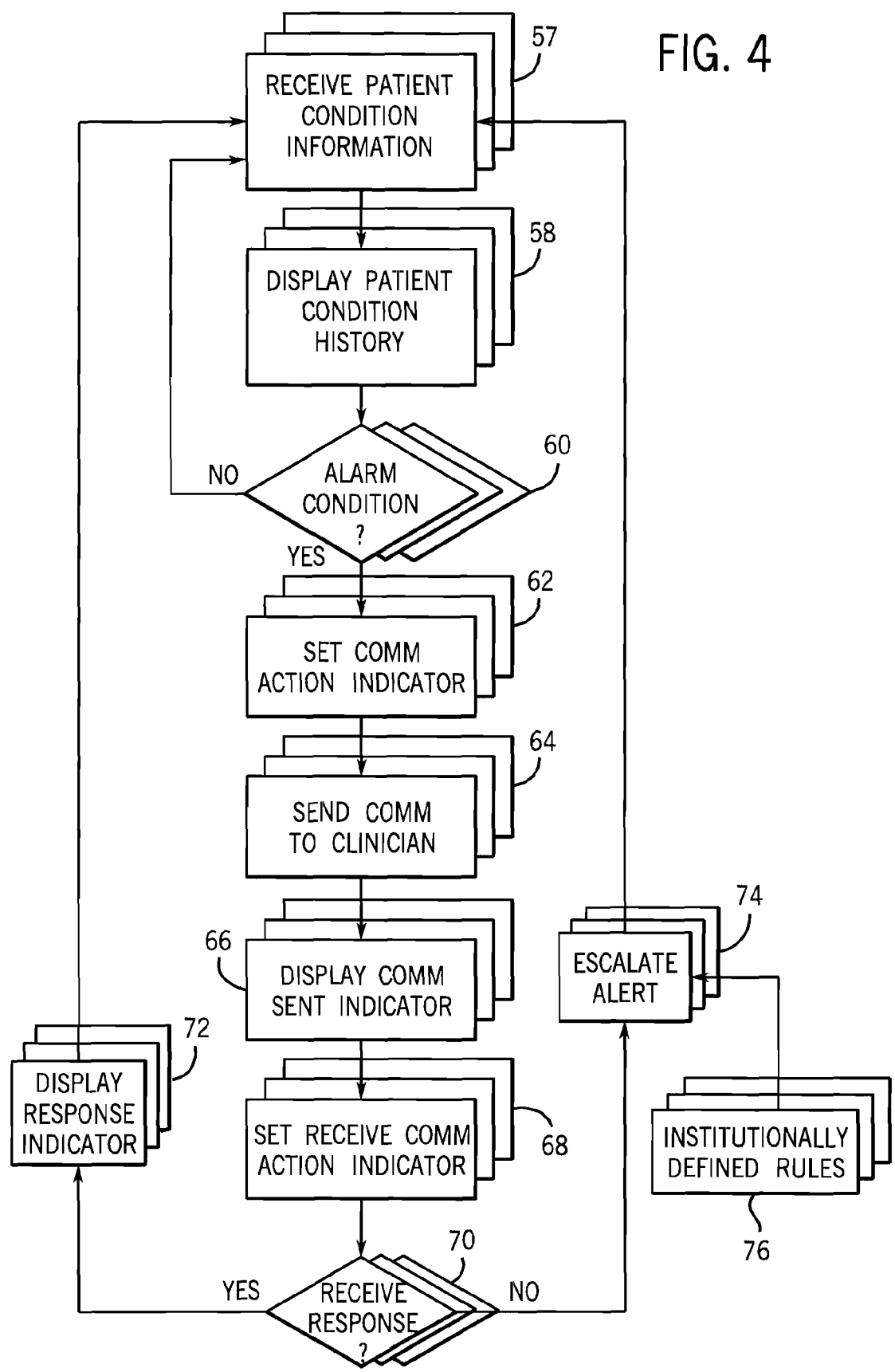
FIG. 4 is a flow chart depicting the steps of an embodiment of the method of the present invention.

FIG. 4 is a flow chart depicting the steps in the method of the present invention. First the technician must receive the patient condition information 57. The information may be transmitted to the technician, who is in a centralized location, in a variety of ways including both wired and wireless technologies. Next, the patient condition history is displayed in step 58 including the new patient condition information that was received in step 57. The technician reviews this patient condition history and determines in step 60 whether or not there is an alarm condition. If there is no alarm condition, then the cycle repeats itself and the technician waits to receive new patient condition information at step 57.

However, if there is an alarm condition, detected in step 60, then a communication action indicator appears on the patient display at step 62. This communication action indicator prompts the technician to send a communication to the proper clinician in step 64. Once the communication has been sent from the technician to the clinician, the monitoring display displays a communication sent indicator in the patient condition history at the time the communication was sent in step 66. Once the communications sent indicator has been set, then the communication action indicator is set to indicate that a communications is to be received next, step 68. The communication sent indicator prompts the technician to determine whether a response has been received in step 70. If a response from the clinician is received, then a response indicator is displayed on the patient condition history in step 72 and the technician then waits to receive new patient condition information at step 56. However, if no response from the clinician to the technician is received, then the patient alarm may be escalated in step 74. The escalation of the alarm in step 74 may be according to a series of institutionally defined rules 76 that are applied to the present patient alarm situation. After the alarm escalation step 74, the technician waits to receive new patient condition information at step 57. Potentially, the patient alarm condition may be corrected before any communication from the clinician is received. If this is not the case, however, then the technician goes through the rest of the communication steps 62-70 under the escalated conditions.

It is understood that in the above method, parts of or entire steps may be performed by a computer workstation that is controlling the monitoring display and rendering the patient condition history. It is further understood that the institutionally defined escalation rules 76 may modify the flow chart in that an institution may add additional communication attempts, or other safeguards before an alarm is escalated. Furthermore, while a technician is used to describe the steps in this embodiment of the method of the present invention, it is understood that any of a variety of health care administrators and/or administrative assistants may be utilizing this method to achieve the same or similar ends.

The system and method of the present invention serves to simplify the cognitive load and formality of process required by the technician currently to handle the large amount of data that is being sent to the central monitoring station, which will reduce errors and improve the coordination between the technicians and the clinicians. Furthermore, with a single informative display and less reliance upon the memory and/or organizational ability of each of the individual technicians, greater continuity of health care support is achieved between shift changes and/or technician breaks. Specifically during a shift change or a technician break, a new technician must jump into the place of the old technician and the system and method of the present invention more readily allows the new technician to jump into the place of the old technician. The system and method of the present invention will allow the new technician to be notified of any patient alarm conditions and what if any communication attempts have been made, as well as which communications have been received back from the clinician.

Finally, by the system and method of the present invention, a greater situational awareness is achieved by the technician, which will promote efficiency by both the technician and the clinicians. The greater situational awareness provided by the system and method of the present invention means that the technician won't have to rely on memory to know the status of each of the communications between the technician and the clinicians. Therefore, additional time on both the parts of the clinician and the technician will not be wasted by the technician making calls that have already been confirmed by the clinician. Also, the greater situational awareness provided to the technician by the system and method of the present invention allows for greater prioritizing of the patient alarms for technician and clinician response. This means that a low priority, but currently unattended alarm will not take precedence over a more critical, but newer alarm simply because the low priority alarm has not been attended to yet.

This written description uses examples to disclose the invention, including the best mode, and also to enable any person skilled in the art to make and use the invention. The patentable scope of the invention is defined by the claims and may include other examples that occur to those skilled in the art. Such other examples are intended to be within the scope of the claims if they have structural elements that do not differ from the literal language of the claims, or if they include equivalent structural elements of insubstantial difference from the literal language of the claims.

Various alternatives and embodiments are contemplated as being with in the scope of the following claims, particularly pointing out and distinctly claiming the subject matter regarded as the invention.

What is claimed is:

1. A method of providing care to a plurality of patients, the patients being attended by a clinician, a patient condition for each of the patients being transmitted to a centralized location, the method comprising the steps of:
   receiving at a centralized location from a monitoring device a signal indicative of the patient condition from each of a plurality of patients;
   displaying a real time-based representation of each patient's condition to a technician on a monitoring display;
   sending a communication from the technician to the clinician via a communication platform upon a change in patient condition;
   displaying in real time on the monitoring display to the technician a record of the communication attempt, wherein the record includes a communication sent indicator;
   displaying to the technician an indication of the next probable action to expect for each of the plurality of patients in a next action column of the monitoring display; and
   displaying to the technician a patient metric in a metrics column, wherein the patient metric is one of an institutionally defined metric or a technician selected metric, further wherein all of the displaying steps occur simultaneously.

2. The method of claim 1 wherein the indication of the next probable action to expect is based upon analysis of normal workflow.

3. The method of claim 1 wherein the change in patient condition is a patient alarm.

4. The method of claim 3 further comprising the step of receiving a communication from the clinician in acknowledgement of the communication from the technician.

5. The method of claim 4 further comprising the step of displaying to the technician a record of the receipt of the communication from the clinician.

6. The method of claim 5 further comprising the step of escalating the alarm if no communication from the clinician is received.

7. A method of providing care to a plurality of patients, the patients being attended to by a clinician, the method comprising the steps of:
   transmitting a patient condition for each of the patients to a centralized location;
   receiving at the centralized location from a monitoring device a signal indicative of the patient's condition from each of the plurality of patients;
   displaying a real time-based representation of each of the patient's conditions on a monitoring display;
   monitoring for a change in the patient condition for any of the plurality of patients;
   sending a communication to the clinician via a communication platform upon a change in patient condition for any of the plurality of patients;
   displaying in real time a record of the communication attempt, wherein the record includes a communication sent indicator;
   displaying an indication of the next probable action to expect for each of the plurality of patients in a next action column of the monitoring display; and
   displaying to the technician a patient metric in a metrics column, wherein the patient metric is one of an institutionally defined metric or a technician selected metric, further wherein all of the displaying steps occur simultaneously.

8. The method of claim 7 wherein the time-based representation of each patients conditions and the record of the communication attempts is displayed upon a display unit having a graphical user interface that simultaneously displays the patient condition for each of the plurality of patients and a communication indicator indicating the times at which a communication has been made to the clinician.

9. The method of claim 7 wherein the communication to the clinician is transmitted utilizing a first communication device.

10. The method of claim 9 further comprising the step of receiving a communication from the clinician in acknowledgement of the receipt of the communication upon a change in patient condition.

11. The method of claim 10 wherein if no response has been received from the clinician, sending the communication to the clinician using a second communication device, wherein the second communication device is different from the first communication device.

12. The method of claim 7 wherein the change in patient condition is the activation of an alarm.

13. The method of claim 10 further comprising the step of displaying a record of the receipt of the communication from the clinician.

14. The method of claim 10 further comprising the step of displaying a record of the receipt of the communication from the clinician.

15. The method of claim 14 further comprising the step of escalating the alarm if no communication from the clinician is received.

16. The method of claim 14 further comprising the step of displaying the time that has elapsed since the communication to the clinician until the clinician has responded.

\* \* \* \* \*